United States Patent [19]

Kourtakis

[11] Patent Number: 5,510,308

[45] Date of Patent: Apr. 23, 1996

[54] CATION AND VANADIUM SUBSTITUTED HETEROPOLYACID CATALYSTS FOR VAPOR PHASE OXIDATION

[75] Inventor: Kostantinos Kourtakis, Hockessin, Del.

[73] Assignee: E. I. Du Pont de Nemours and Company, Wilmington, Del.

[21] Appl. No.: 325,840

[22] Filed: Oct. 19, 1994

[51] Int. Cl.$^6$ .............................. B01J 27/18; B01J 27/19; B01J 27/198; C07D 307/34

[52] U.S. Cl. ............................................. 502/209; 549/259

[58] Field of Search ............................. 502/209; 549/259

[56] References Cited

U.S. PATENT DOCUMENTS

| | | | |
|---|---|---|---|
| 4,147,661 | 4/1979 | Higgins et al. | 252/435 |
| 4,192,951 | 3/1980 | Slinkard et al. | 562/549 |
| 4,668,802 | 5/1987 | Contractor | 549/259 |
| 5,070,061 | 12/1991 | Langerbeins | 502/211 |
| 5,215,952 | 6/1993 | Bielmeier et al. | 502/209 |

FOREIGN PATENT DOCUMENTS

| | | | |
|---|---|---|---|
| 59-36546 | 2/1984 | Japan | B01J 27/18 |
| 59-19545 | 2/1984 | Japan | B01J 27/18 |

OTHER PUBLICATIONS

Tsigdinos, G. A., "Heteropoly Compounds of Molybdenum and Tungsten", *Topics in Current Chemistry*, Springer-Verlag, Berlin (1978). Date of publication not provided Tourne', C. M. et al, *C.R. Acad Sci. Paris*, 266 1363–1365 (1968) (Translation included). Date of publication not provided.

Weakley, T. J. R. et al, *J. Inorg. Nucl. Chem.*, 29, 2935–2944 (1967). Date of publication not provided.

Ai, M., *J. of Catalysis*, 85, 324–330 (1984). Date of publication not provided.

Ai, M., *Tokyo Institute of Technology*, (Int. Cong. Catal. [Proc.]) 8th, vol. 5, 475–486. Date of publication not provided.

Patrut, A. et al, *Stud. Univ. Babes–Bolyai, Chem.* 35(1), 59–74; 68–73 (1990). Date of publication not provided.

*Primary Examiner*—Nicholas Rizzo
*Assistant Examiner*—King L. Wong

[57] ABSTRACT

This invention relates to heteropolyacids characterized by their comprising phosphorus as the heteroatom and molybdenum and/or tungsten at octahedral sites, some of the molybdenum and/or tungsten having been replaced with vanadium and at least one transition metal or main group cation, the vanadium and cation occupying the octahedral sites surrounding the phosphorus heteroatom in the heteropolyacid structure. This invention also concerns the use of these heteropolyacids as catalysts in the oxidation of n-butane to maleic anhydride.

9 Claims, 2 Drawing Sheets

CATION AND VANADIUM SUBSTITUTED HETEROPOLYACID CATALYSTS FOR VAPOR PHASE OXIDATION

FIELD OF THE INVENTION

This invention relates to heteropolyacids characterized by their comprising phosphorus as the heteroatom and molybdenum and/or tungsten at octahedral sites, some of the molybdenum and/or tungsten having been replaced with vanadium and a transition metal or main group cation. This invention also concerns the use of these heteropolyacids to oxidize n-butane to maleic anhydride and their use as lattice oxygen catalysts.

TECHNICAL BACKGROUND

Maleic anhydride is used as a raw material for products ranging from agricultural chemicals, paints, paper sizing and food additives to synthetic resins. To fill the high demand for this valuable chemical, a variety of commercial processes have been developed.

One important route to maleic anhydride involves the vapor phase oxidation of n-butane over a vanadiumphosphorus oxide catalyst. The reaction step involves oxidation of n-butane with air (oxygen) to form maleic anhydride, carbon oxides, water and smaller amounts of partially oxidized by-products. Typically, the process is carried out in fixed-bed reactors, fluid-bed reactors, or more recently in recirculating solids reactors having two reaction zones in which two separate reactions take place with a catalyst (the solid) circulating between the two reaction zones and taking part in reactions in both zones.

U.S. Pat. No. 4,192,951 ('951) discloses a vapor phase process for the oxidation of 4-carbon hydrocarbons to maleic acid and acetic acid with a molybdenum heteropolyacid catalyst. Disclosed catalysts include those in which the central phosphorus atom in heteropolyacids such as $H_3PMo_{12}O_{40}$ is replaced with various transition metals, Si and Ge. The phosphorus atom is the heteroatom and occupies the tetrahedral site at the center of the heteropolyacid cluster. There is no disclosure of a heteropolyacid where the molybdenum is replaced by vanadium and a transition metal or main group cation.

The lattice oxygen of a vanadium phosphate catalyst is described in U.S. Pat. No. 4,668,801 wherein a vanadium phosphate catalyst is used for n-butane oxidation. Improvements such as an increase in selectivity are described for cases where a sub-stoichiometric amount of oxgen is used, or no oxygen is used over a vanadium phosphate catalyst in a recirculating solids reactor.

There are heteropolyacids described in the literature though most are characterized in solution, as opposed to the solid phase, or are characterized in the solid phase as the completely neutralized alkali salt. That is, all of the Brönsted acidity is neutralized in these salts which form as a precipitate. This makes the material essentially or nearly inactive for n-butane oxidation catalysis.

There is also mentioned in the literature the addition of secondary ions to preformed heteropolyacids. For instance, in Japanese Patent Application SHO JP59-36546, a catalyst system for n-butane oxidation is described containing $H_3PMo_{12}O_{40}$ to which a secondary salt is added. For this catalyst system, copper and/or cesium and vanadium are placed on the outside of the heteropolyacid cluster, i.e., not on octahedral sites, but instead are part of a secondary structure where they neutralize some of the Brönsted acid sites, replacing $H^+$ or $H_3O^+$. These secondary metals are not part of the primary cluster structure.

In spite of the progress in catalyst and process development over the years, a need still remains to continue to improve heteropolyacids useful in the oxidation of n-butane to maleic anhydride, and it is to that end that the present invention is directed.

SUMMARY OF THE INVENTION

This invention provides a heteropolyacid catalyst for the oxidation of n-butane to maleic anhydride comprising a crystalline oxide of formula I or formula II:

$$H_nPM_{12-x-y}V_xA^z_yO_{40} \qquad (I)$$

$$H_nP_2M_{18-x-y}V_xA^z_yO_{62} \qquad (II)$$

wherein:

P is a heteroatom;

M is at least one metal in the +6 oxidation state selected from Mo and W, said metal occupying an octahedral site surrounding the phosphorus atom;

x is an integer selected from 1, 2 and 3;

y is an integer selected from 1, 2 and 3;

A is at least one cation selected from the group consisting of Li, Mg, Sc, Ti, Cr, Mn, Fe, Co, Ni, Cu, Zn, Zr, Nb, Ru, Rh, Pd, Ta, Re, Os, Ir, Pt, Al, Ga, Ge, Sn, Pb, As, Sb, Bi, Po, Tb, and Pa, said cation occupying an octahedral site surrounding the phosphorus atom;

z is a number from 1–6 representing a weighted average of the oxidation states of all of the A cations; and n is a number calculated as follows: in formula I: $n=3-yz+x+6y$, and in formula II: $n=6+x+6y-yz$.

This invention further provides an improved process for the oxidation of n-butane to maleic anhydride comprising contacting n-butane with a source of oxygen in the presence of a heteropolyacid catalyst of formula I or formula II as defined above. The catalyst can be the only source of oxygen.

DETAILED DESCRIPTION OF THE INVENTION

This invention provides a heteropolyacid catalyst for the oxidation of n-butane to maleic anhydride comprising a crystalline oxide of formula I or formula II:

$$H_nPM_{12-x-y}V_xA^z_yO_{40} \qquad (I)$$

$$H_nP_2M_{18-x-y}V_xA^z_yO_{62} \qquad (II)$$

wherein:

P is a heteroatom;

M is at least one metal in the +6 oxidation state selected from Mo and W, said metal occupying an octahedral site surrounding the phosphorus atom;

x is an integer selected from 1, 2 and 3;

y is an integer selected from 1, 2 and 3;

A is at least one cation selected from the group consisting of Li, Mg, Sc, Ti, Cr, Mn, Fe, Co, Ni, Cu, Zn, Zr, Nb, Ru, Rh, Pd, Ta, Re, Os, Ir, Pt, Al, Ga, Ge, Sn, Pb, As, Sb, Bi, Po, Tb, and Pa, said cation occupying an octahedral site surrounding the phosphorus atom;

z is a number from 1–6 representing a weighted average of the oxidation states of all of the A cations; and n is a number calculated as follows: in formula I: n=3−yz+x+6y, and in formula II: n=6+x+6y−yz.

A can be a combination of elements. In those cases where there is more than one A, z is the weighted average oxidation state of those elements, a number from 1–6.

Preferably M is Mo.

Preferred A's are Cu, Mn, Ni, Zn, Co, Sb, Bi, Pb, Fe, Pa, Pd and As. More preferred A's are Cu, Mn, Ni, Zn, Co, and Sb. Cu is most preferred. It is preferred that each A within a single compound is the same.

Preferred x and y are 1.

Examples of specific catalysts of formula I and formula II comprise:

Heteropolyacids of the present invention are typically prepared in an aqueous solution, generally after acidifying and heating the reactants. The reactants comprise oxides of molybdenum and/or tungsten, and vanadium, for example, $MoO_3$ and $V_2O_5$, or in some cases, the ammonium or sodium salts of molybdic acid, vanadic acids or tungstic acids, in addition to compounds containing the "A" cation of choice, for example, the oxides or acetylacetonates, chlorides or acetates of Li, Mg, Sc, Ti, Cr, Mn, Fe, Co, Ni, Cu, Zn, Zr, Nb, Ru, Rh, Pd, Ta, Re, Os, Ir, Pt, Al, Ga, Ge, Sn, Pb, As, Sb, Bi, Po, Tb and Pa. Examples of compounds containing the "A" cation of choice comprise CuO, $ZnCl_2$, Co (II) acetylacetonate, Ni (II) actylacetonate, and Mn (II) acetylacetone (Mn (II) 2,4-pentanedionate). Normal commercially available reagents are used for the reactants. The highest purity products attainable need not be employed; however the purity of the reagents must be known in order to calculate the gross amount required. In addition, the reagents should not be contaminated with any catalyst poison. The amount of reagent employed should be within plus or minus 5%, preferably within plus or minus 2% of the amount indicated by stoichiometry. Amounts of the appropriate reactants are calculated to give the desired heteropolyacid of formula I or formula II.

The reactants are combined in water and heated to elevated temperatures. A convenient temperature is reflux (100° C). Aqueous $H_3PO_4$ is added slowly until the desired stoichiometry is achieved. Reflux is continued; a convenient time is overnight, but time and temperature are not critical as long as the time/temperature is sufficient for all of the reagents to go into solution and give a clear, usually highly colored, solution. In some cases the reaction is complete within two hours at reflux, in other cases longer time is required.

The reaction can be carried out conveniently under air atmosphere. Inert atmospheres can also be employed. The process is usually conducted at normal atmospheric pressure, but elevated or reduced pressures can be employed. Agitation is not required, but is usually provided to facilitate heat transfer.

Glass and stainless steel are usually employed as material of construct. This is not critical as long as materials that contaminate the product with catalyst poisons are not employed.

The product, a crystalline oxide, is isolated by evaporating the reaction mixture to dryness. This can be carried out by any known method, typically employing an applied vacuum to speed the process. The isolated product can be used as is, or in cases where size and shape of the catalyst is dictated by the requirements of the equipment employed in the subsequent use of the heteropolyacid, the product heteropolyacid can be processed or fabricated into various size and shape particles before use by grounding, pelletizing, briquetting, tabulating, or shaping in other ways as required.

Variants of the above described preparative procedure include a method for making the ammonium salts of the desired heteropolyacid followed by a drying step and decomposition of the ammonium salts in flowing nitrogen at elevated temperatures (below 450° C.).

A second alternate preparation route is to generate the desired acid form of the heteropolyacid via ion exchange of the ammonium or sodium salts. This can be accomplished by contacting them with a sulfonic ion exchange resin, such as DOWEX HCRW-2 (Dow Corp., Midland, Mich.). An alternative is to acifidy a solution of the ammonium or alkali salts with a mineral acid, such as sulfuric acid. The heteropolyacid is then extracted with ether to form the corresponding etherate, which is then dried to form the free heteropolyacid.

The method of preparing the heteropolyacids of the present invention, as described above, is significantly different from methods in the art used to prepare different catalysts, in that in those methods a transition metal is added to an already formed heteropolyacid. X-ray single crystal diffraction data show that the basic structure of heteropolyacids of formula I and formula II of the present invention is that of a Keggin anion with hydronium cations and water molecules of solvation. By the term "heteropolyacid" is meant a class of heteropoly electrolytes which comprise 2 to 18 hexavalent molybdenum or tungsten atoms which surround one or more central atoms (heteroatoms). Phosphorus is the tetrahedrally coordinated heteroatom of the present invention and is located at the center of the heteropolyacid crystalline cluster. This central heteroatom is buried by surrounding octahedral or pendant ion sites which are occupied by molybdenum and/or tungsten, vanadium and at least one cation "A" atom which is a transition metal or main group cation other than molybdenum or tungsten. Thus, some of the sites in the crystal lattice which would normally be occupied by molybdenum or tungsten, are occupied by atoms of vanadium or "A" cations in the heteropolyacids of formula I or formula II. These anion structures can be represented by polyhedra that share corners or edges with one another. Each molybdenum and/or tungsten, and vanadium and "A" cation are at the center of an octahedron, and an oxygen atom is located at each vertex of the octahedron. When two octahedron share an edge, this means that two particular oxygen atoms form part of each octahedron. The central heteroatom is similarly located at the center of a tetrahedron. Each such polyhedron containing the central heteroatom is generally surrounded by octahedra, which share corners with it and corners and edges with one another so that the correct total number of oxygen atoms is utilized. Each surrounding octahedron is directly attached to the central heteroatom through a shared oxygen atom.

The presence of phosphorus which occupies the central tetrahedral site is necessary for active and selective butane oxidation catalysts. Replacing some of the molybdenum and/or tungsten with vanadium is needed to make an active and selective catalyst for n-butane oxidation. According to the present invention, in addition to the vanadium substitution, substitutions of molybdenum and/or tungsten with at least one other cation occurs on the octahedral sites. This results in different compositions which display different activity from those which occur with substitutions at other sites, for example, on sites outside of the primary cluster, forming part of a secondary structure which can link clusters together. From a purely geometric viewpoint, changes in the outer, octahedral ions can directly affect interaction with butane since these outer atoms form the surface of the crystalline cluster, through bonding with the oxygens, and therefore of the catalyst. In addition, by substituting on the octahedral sites in the heteropolyacid, protons are added or subtracted to form a charge-neutral fully oxidized cluster. In this sense, the substitutional chemistry directly influences the acid site density of the solid material. In cases where the cation substitution for molybdenum and/or tungsten is less than hexavalent, the number of Brönsted sites for the fully oxidized cluster will increase. This method of introducing a transition metal or main group cation substituent is very different from those in the art where a cation is simply added to the outside of a preformed heteropolyacid, because in those cases the added cation will neutralize some of the Brönsted acid sites.

The catalysts of the present invention, once formed, can be partly or fully neutralized to a salt form. Some of the partially neutralized heteropolyanion salts can be employed as catalysts. These salts typically comprise alkali metal or alkaline earth cations.

The heteropolyacids of the present invention are useful as catalysts in the oxidation of n-butane in the presence of oxygen. In addition, the heteropolyacids of the present invention are useful as lattice oxygen catalysts in the oxidation of n-butane with the ability to selectively oxidize n-butane in the absence of gas phase oxygen.

The catalysts of the present invention can be used alone, supported on a catalyst support or impregnated in a carrier material. Typical support/carrier materials are well known to those skilled in the art as are methods of preparing supported or impregnated catalysts. Typical materials comprise silica, titania, zirconia, alumina, thoria, silicon carbide, and carbon.

This invention provides an improved process for the oxidation of n-butane comprising contacting n-butane with a source of oxygen in the presence of a heteropolyacid catalyst of formula I or formula II.

Although the process of the invention is embodied in the following laboratory scale examples, Applicant notes that the invention can be practiced on an industrial scale by making the necessary engineering and design modifications which are customary in the art.

Prior to use, the catalyst of formula I or formula II is typically formed into a convenient catalyst shape by pelletizing the catalyst typically at about 30,000 psi ($2.07 \times 10^6$ kPa) or less, to form small disks and crushing the pellet through sieves. For fixed bed reactor evaluations, typically a −40, +60 mesh is used (U.S. Sieve Series). Optionally, one could blend the resultant powder with 1–3% of a die lubricant and pellet binder, such as graphite or Sterotex®, a hydrogenated cottonseed oil, commercially available from Capital City Products Company, Columbus, Ohio, before tabletting. For fluidized bed reactor use, the preferred size range is 20 to 150 micrometers.

The catalyst of the present invention can be utilized advantageously with regard to conversion and selectivity in the wide variety of conventional techniques and reactor configurations employed to conduct the vapor phase oxidation of n-butane to maleic anhydride. For example, the conversion can be conducted in a fixed-bed reactor, whereby the catalyst particles are maintained in a fixed position and are contacted with n-butane and a source of oxygen, typically molecular oxygen, both in appropriate amounts, optionally in the presence of one or more inert diluent gases, at a temperature varying between 200° C. and about 450° C., preferably between about 300° C. and about 350° C. The greatest advantages of using the catalyst of this invention are realized when the conversion of n-butane to maleic anhydride is carried out in a recirculating solids reactor, such as that described in U.S. Pat. No. 4,668,802. This patent discloses an improved process for the selective vapor phase oxidation of n-butane to maleic anhydride over a vanadium/phosphorus/oxygen (VPO) catalyst, whereby the amount of oxygen in the feed gas to the VPO catalyst is limited to less than the stoichiometric amount required for the total amount of n-butane converted in the process. The reduced catalyst resulting from the oxidation is separated from the gaseous product stream; and is reoxidized, optionally in a separate reaction zone, before being contacted with n-butane.

While the present invention is not bound by theory, it is believed that the increased oxygen capacity of the catalyst of this invention allows this catalyst to effectively catalyze high conversion to maleic anhydride, even under conditions where the catalyst is reduced or is the only source of oxygen for n-butane. This behavior is contrasted with prior art catalysts and promoted catalysts, such as that described in U.S. Pat. No. 4,442,226, wherein the VPO or promoted VPO catalysts are sensitive to the partial pressure of oxygen with respect to their catalytic activity, and it is recommended that the partial pressure of oxygen in the feed be maximized within the limits of safe operability. Use of the catalyst of the present invention, consequently, provides advantages in safety of operation as well as conversion, because one can operate at lower levels of oxygen in the feed which will mitigate the explosion hazard.

Maleic anhydride capacity can be determined by an evaluation of a catalyst in 1.5% butane/nitrogen, conditions under which oxygen from the catalyst lattice oxidizes butane. In testing for maleic anhydride capacity, the catalyst is reduced for a certain length of time. The total amount of maleic anhydride produced during one such cycle is measured as micromoles produced per gram of catalyst. Comparative Example I describes such testing over the course of 99 minutes for a VPO standard laboratory catalyst and the catalyst, $H_nPMo_{10}VCuO_{40}$, of the present invention. Results shown in FIG. 2 demonstrate a maleic anhydride signal lasting the full time period unlike the VPO catalyst. Maleic anhydride capacity results for various heteropolyacids are shown in Table III and Table IV. For many of the vanadium phosphate-like compositions found in the art, the amount of maleic anhydride produced by the end of the 99 minute protocol is essentially zero.

Figure 1:
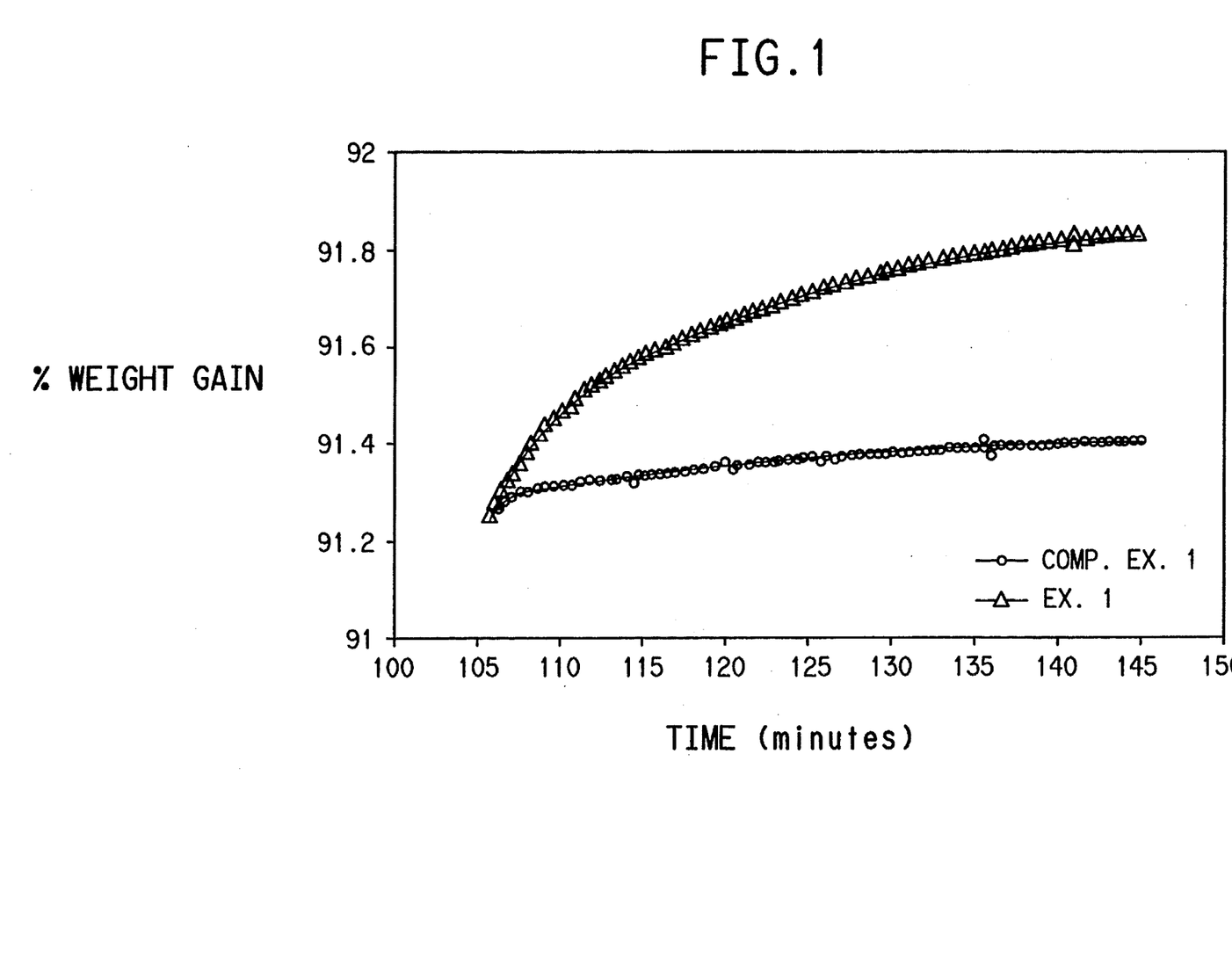
FIG. 1 is a graph of the percent weight gain of two catalysts versus time in minutes as described in Comparative Example I. The top line labelled with a triangle represents catalyst of the present invention, $H_nPMo_{10}VCuO_{40}$ prepared as described in Example 1. The bottom line labelled with a circle represents a vanadium phosphorus oxide (VPO) catalyst prepared as described in Comparative Example I.

Catalysts of the present invention demonstrate an ability to reoxidize more fully after reduction in butane than VPO laboratory standard catalysts as shown in FIG. 1. This ability to reoxidize renders the catalysts of the present invention particularly valuable as lattice oxygen catalysts in the oxidation of n-butane to maleic anhydride in the absence of oxygen or in processes where a sub-stoichiometric amount of oxygen is present.

The catalyst of the present invention also demonstrates good results in activity and conversion and selectivity. Tables I and II below show selectivity at 40% conversion for various catalysts of the present invention and compare these results with those of other catalysts in the art. Catalysts of formula I or formula II wherein A is copper or copper and antimony show particularly good results.

Examples

For the catalysts prepared to illustrate this invention, for example the catalyst of Example 1, it is believed that more than one oxidation state of the transition metal may be present. That is, the copper, although believed to be predominantly in oxidation state 2, may be partially in oxidation state 1, or an intermediate value. Therefore, a range of formulae for the heteropolyacids that could result when copper is incorporated are given. This is done for all examples where applicable. Where more than one "A" cation is present, the extreme values of n are determined by the various combinations of oxidation states possible for said "A" cations. For the product of Example 10, where Sb and Cu are present, z has the following extreme values: Sb +3, Cu +1, z=2; and Sb +5, Cu +2, z=3.5. The corresponding extreme values of n, calculated from the formula n=6+x+6y−yz are, respectively, 16 and 13.

Example 1

Preparation of $H_nPMo_{10}VCuO_{40}$
(Formula I, $H_nPM_{12-x-y}V_xA_y^zO_{40}$ wherein M=Mo, A=Cu, x=1, y=1, z is 1–2, predominantly 2, and n=8–9)

1000 mL of water is added to a 3 liter round bottom flask equipped with an addition funnel, mechanical stirrer and a reflux condenser. 100.2 g $MoO_3$ (Cerac Chemicals, Milwaukee, Wis.), 6.33 g vanadium pentoxide ($V_2O_5$, Alfa Chemicals, Ward Hill, Mass.) 5.5 g CuO (Fluka Chemicals, Ronkonkoma, N.Y.) is added and the slurry is brought to reflux. Aqueous phosphoric acid (85%, J. T. Baker, Phillipsburg, N.J.) is then slowly added over the course of 20 minutes, until the desired stoichiometry is achieved. After about 3 hr, an orange-red solution forms. Typically, the reflux was continued for 16 hours (overnight). The samples are dried at 120° C. for approximately 12 hours in nitrogen.

Single crystals of this material were formed by creating a saturated or supersaturated solution. Approximately 15.9 g were dissolved in 5.5 mL of water. Crystallization occurred over the course of about 2 weeks at room temperature. The crystals formed as large, red-orange crystals with cubic morphology. Inductively Coupled Plasma (ICP) results of the mother liquor and the single crystal indicate almost identical stoichiometries for the two.

A microprobe analysis taken on the same crystal which was used for the data collection gave $Mo_{9.9}/V_{0.9}/Cu_{1.2}$. The basic structure is that of a Keggin anion with hydronium cations and water molecules of solvation. There is only one metal site in this structure and its occupancy/multiplicity refined to a value of 0.456(6) based on the Mo scattering factor; the expected ratio for a 10:1:1 mix of metals would be 0.468. Both the Cu and the V have thus been included in the Keggin anion with the Cu atom occupying octahedral sites in the Keggin anion, as do the molybdenum and vanadium atoms.

Example 2

Micro-reactor Evaluation of Catalyst of Example 1 in Butane Oxidation

The sample was pelletized at $1.38\times10^6$ kPa into disks and subsequently crushed and sieved through (−40, +60) mesh screens. About 1 g of catalyst is used for the reactor evaluations.

The micro reactor consisted of a 40.64 cm by 0.64 cm stainless steel tube enclosed by an aluminum sheath (3.12 cm thick, to assist in minimizing thermal gradients) which itself was enclosed in a tube furnace. The reactor was mounted vertically with the direction of the gas flow from top to bottom. Pressure gauges were mounted near both the entrance and exit of the reactor to monitor pressure changes. A bypass valve installed near the reactor entrance allowed the entering gas stream to pass through either the reactor or to bypass the reactor and pass directly to the sampling valve system, allowing analysis of the reactor feed gases prior to reaction. A tee connection at the top of the reactor allowed a thermocouple to be mounted to monitor the temperature at the entrance to the packed catalyst bed. Commercially available mass flow meters (Tylan Model FC-260, available from Tylan Corp., Torrance, Calif.) of ranges 0–100 and 0–10 cc/minute, respectively, fed the reactor. The heated exit gas stream (200° C.) passed through a heated sampling valve allowing the selection of a gas sample (250 µl) of the stream for analysis by gas-liquid chromatography (GLC), using a commercially available instrument (Gow-Mac Series 740P FID GLC available from Gow Mac Corp., Bridgewater, N.J.). The GLC was used to analyze for butane and for the products maleic anhydride, acetic acid and acrylic acid.

The pseudo-first order rate constant, k, given for the disappearance of butane in Table I and Table II below was obtained by fitting the reactor data to a classical first order rate expression:

$$d[butane]/dt = -k[butane]$$

$$d(xo-x)/dt = -k(xo-x)$$

wherein
 xo=initial conc. of butane
 x=portion of butane reacted
Integrating this expression gives the concentration of butane exiting the reactor as a function of contact time, t, in the reactor:

$$[exit\ butane] = xo-x = xo*\exp(-kt)$$

In addition to describing the reaction rate of butane with a catalyst, the rate constant k includes several other factors including the dependence of the reaction rate on oxygen concentration, which remains relatively constant under these conditions, and the concentration of catalyst active sites which are also assumed constant.

The catalysts listed in Tables I and II below were evaluated as described above for Example 1.

Example 3

Preparation of $H_8PMo_{10}VZnO_{40}$
(Formula I, $H_nPM_{12-x-y}V_xA_y^zO_{40}$ wherein M=Mo, A=Zn, x=1, y=1, z=2, and n=8)

The procedure described in Example 1 was followed, except that in place of the copper oxide, 9.5 g zinc dichloride was used. Crystals grown adopted a structure common to heteropolyanions, namely the cubic, Fd3m, form. The metal atoms were disordered over the 12 sites. A microprobe analysis of the crystal gave the following results: Mo (10.56), V (0.59), Zn (0.85). The metal site was refined using the scattering factor for Mo. Based on the microprobe analysis, its occupancy factor should have refined to 0.479; the x-ray result was 0.463(15). The two numbers agree within experimental error. The microprobe errors for V and Zn were on the order of 10% and 3%, respectively. Although this structure was disordered, it was clear that the vanadium and zinc atoms reside within the heteropolyanion on the octahedral sites occupied by Mo and V.

Example 4

Preparation of $H_8PMo_{10}VCoO_{40}$
(Formula I, $H_nPM_{12-x-y}V_xA_y^zO_{40}$ wherein M=Mo, A=Co, x=1, y=1, z=2, and n=8)

The procedure described in Example 1 was followed, except that in place of the copper oxide, 17.88 g of Co (II) acetylacetonate (available from Johnson-Matthey, Alfa Products, Ward Hill, Mass.) was used.

Example 5

Preparation of $H_8PMo_{10}VNiO_{40}$
(Formula I, wherein $H_nPM_{12-x-y}V_xA_y^zO_{40}$ wherein M=Mo, A=Ni, x=1, y=1, z=2, and n=8)

The procedure described in Example 1 was followed, except that in place of the copper oxide, 20.4 g of Ni (II) acetyl acetonate (Ni (II) 2,4 pentane dionate, available from Johnson-Matthey, Ward Hill, Mass.) was used.

Example 6

Preparation of $H_nPMo_{10}VMnO_{40}$
(Formula I, $H_nPM_{12-x-y}V_xA_y^zO_{40}$ wherein M=Mo, A=Mn, x=1, y=1, z=1-6, and n=4-9)

The procedure described in Example 1 was followed, except that in place of the copper oxide, 17.62 g of Mn (II) acetylacetone (Mn (II) 2,4 pentanedionate, Alfa Chemicals, Ward Hill, Mass.) was used.

Example 7

Preparation of $H_nP_2Mo15V2CuO62$
(Formula II, $H_nP_2Mo_{18-x-y}V_xA_y^zO_{62}$ wherein M=Mo, A=Cu, x=2, y=1, z=1-2, and n=12-13)

The experimental setup was identical to the one described in Example 1. To 1000 ml of water, 115.15 g of $MoO_3$ (Johnson Matthey, Ward Hill, Mass.), 9.09 g of vanadium pentoxide (Alfa Chemicals, Ward Hill, Mass.) and 4.0 g of copper oxide (Fluka Chemicals, Ronkonkoma, N.Y.) was added. 11.53 g of 85% aqueous phosphoric acid (EM Sciences, Gibbstown, N.J.) was then slowly added. After several hours, a red-orange solution formed.

Example 8

Preparation of $H_nPMo_9VCu_2O_{40}$
(Formula I, $H_nPM_{12-x-y}V_xA_y^zO_{40}$ wherein M=Mo, A=Cu, x=1, y=2, z=1-2, and n=12-14)

A procedure similar to that used in Example 1 was followed. In a 3 l flask, 1000 ml of water, 11.1 g of copper oxide (Fluka Chemicals), 90.18 g of $MoO_3$ (Johnson-Matthey/Alfa) and 6.33 g of $V_2O_5$ (Alfa) were added. 8.01 g of aqueous phosphoric acid, 85% (EM Sciences) was then added, and the solution was brought to reflux, following which an orange brown solution was formed.

Example 9

Preparation of $H_nPMo_9V_2CuO_{40}$
(Formula I, $H_nPM_{12-x-y}V_xA_y^zO_{40}$ wherein M=Mo, A=Cu, x=2, y=1, z=1-2 and n=9-10)

Into a 3 l flask, 79.45 g of ammonium molybdate $((NH_4)_6Mo_7O_{24} \cdot 4 H_2O$, J. T. Baker) was dissolved in 500 ml of water. In a separate beaker, 11.698 g of ammonium metavanadate $(NH_4VO_3$, Johnson-Matthey/Alfa) was added to 500 ml of water, and was dissolved while heating. The first two solutions were combined, at which time 3.98 g of copper oxide (CuO, Fluka Chemicals) and 6.603 g of ammonium phosphate $((NH_4)_2HPO_4$, Fisher) was added. 170 ml of 30% ammonium hydroxide (Fisher) was also added, forming a solution which was then exchanged with Dowex HCRW-2 resin (final pH=1.94) to form the red orange solution, which was subsequently dried at 170° C. in nitrogen.

Example 10

Preparation of $H_nP_2Mo_{14}SbV_2CuO_{62}$
(Formula II, $H_nP_2M_{18-x-y}V_xA_y^zO_{62}$ wherein M=Mo; A=Sb, Cu; x=2; y=2; z=2.0-3.5; and n=13-16)

Into a 3 l flask, 1402.28 g of $MoO_3$, 12.7 g of vanadium pentoxide (Alfa), 5.55 g of copper oxide, CuO (Fluka), 15.9 of antimony trichloride, $SbCl_3$ (anhydrous, Johnson-Matthey, ALFA), and 16.02 g of 85% phosphoric acid, EM Sciences, were added and brought to a reflux. A green solution/slurry was formed, which was then dried as described in Example 1 to form the final catalyst.

Comparative Example A

Preparation of $H_3PMo_{12}O_{40}$–$Cu_{0.03}/2V$

Example 1 from Japanese Patent 57-143433 was reproduced as closely as possible from Practical Example 1. The intended stoichiometry was $H_3PMo_{12}O_{40}+2VO^{2+}+0.03$ $Cu^{2+}$. 11.7 g of ammonium vanadate (Johnson-Matthey, Ward Hill, Mass.) was heated to boiling in 200 ml of $H_2O$. In a separate beaker, 31.5 g of oxalic acid $(H_2C_2O_4 \cdot 2H_2O$ was added to 100 ml of $H_2O$ until it went into solution. The two solutions were combined to make a vanadyl oxalate solution. 91.3 g of phosphomolybdic acid (Aldrich Chemicals, Milwaukee, Wis.) was dissolved in 100 ml of water and 0.30 g of copper acetate $(Cu(CH_3COO)_2 \cdot H_2O$, Fisher, Pittsburgh, Pa.). The vanadium oxalate solution was then added to the phosphomolybdic acid/cupric acetate solution to produce a green slurry. 400 g of pumice powder (EM Sciences, Gibbstown, N.J.) was added and mixed into the slurry. The material was evaporated to dryness and calcined at 360° C. for 5 hours in flowing oxygen.

Comparative Example B

Preparation of $H_4PMo_{11}VO_{40}$ by Reflux

To a five liter, three neck round bottom flask (fitted with a heating mantle for refluxing), 440.9 g of molybdenum oxide ($MoO_3$, Johnson-Matthey, Ward Hill, Mass.), 25.3 g of vanadium oxide ($V_2O_5$, Alfa Chemicals, Ward Hill, Mass.) 32.0 g of 85 wt % phosphoric acid (EM Sciences, Gibbstown, N.J.) was added. After about 16 hours of reflux, a red-brown solution formed. The material was evaporated to dryness to produce the free acid.

Comparative Example C

Preparation of Cu+$H_4PMo_{11}VO_{40}$

Close to one equivalent of copper was added to a heteropolyacid solution of Example B. 4.45 g of $H_4PMo_{11}VO_{40}$, from Example B, was dissolved in 50 ml of water. $CuCO_3 \cdot Cu(OH)_2$ (Mallinckrodt, Paris, Ky.) was added to neutralize one of the four Bronsted acid sites (effervescence was observed during the addition, indicating release of $CO_2$). Because of waters of hydration associated with the Cu reagent and with the heteropolyacid, the amount of added Cu reagent was adjusted and checked by ICP (inductively coupled plasma) analysis to obtain the correct stoichiometry. In our case, we added 0.29 g of the copper reagent, but the amount needed may vary depending on the degree of hydration. The final cation stoichiometry, as determined by this technique, was "$Cu_{0.96}P_1V_{0.943}Mo_{11.07}$".

Comparative Example D

Preparation of $H_4PMo_{11}VO_{40}$ by Exchange of Sodium Salts

The procedure of U.S. Pat. No. 4,192,951 was used to prepare a catalyst of composition $H_4PMo_{11}VO_{40}$. 33.5 g of sodium phosphate, dibasic ($Na_2HPO_4 \cdot 7 H_2O$, Aldrich Chemicals, Milwaukee, Wis.) was dissolved in 100 ml of $H_2O$, after bring to reflux. A second solution containing 16.2 g of sodium metavanadate ($NaVO_3$, Alfa Chemicals, Ward Hill, Mass.) in 150 ml $H_2O$ was prepared. A third solution containing 3.33 g of sodium molybdate ($Na_2MoO_4 \cdot 2 H_2O$, Fisher, Pittsburgh, Pa.) in 500 ml of water. The three solutions were then combined. This was then added to a 250 ml separatory funnel. The heteropolyacid was separated by adding ether, to make the appropriate etherate, which was then removed and dried to make the free acid.

Comparative Example E

Preparation of Cu+$H_4PMo_{11}V_1O_{40}$

Close to one equivalent of copper was added to a heteropolyacid solution of Example D. 4.45 g of $H_4PMo_{11}VO_{40}$, from Example D, was dissolved in 50 ml of water. $CuCO_3 \cdot Cu(OH)_2$ (Mallinckrodt, Paris, Ky.) was added to neutralize one of the Bronsted acid sites (effervescence was observed during the addition, indicating the release of $CO_2$). Because of waters of hydration associated with the Cu reagent and with the heteropolyacid, the amount of added Cu reagent was adjusted and checked by ICP (inductively coupled plasma) analysis to obtain the correct stoichiometry. In this case, 0.197 g of the copper reagent was added but the amount needed may vary depending on the degree of hydration. The final stoichiometry, as determined by this technique, was $H_xCu_{0.89}P_{1.0}Mo_{11.8}V_{1.08}$.

Comparative Example F $H_3PMo_{12}O_{40}$

Commercially available $H_3PMo_{12}O_{40}$ was used. The supplier is Aldrich, Ward Hill, Mass., catalog no. 22,185-6.

Comparative Example G $Cs_4PMo_{11}VO_{40}$ 4.5 g of the $H_4PMo_{11}VO_{40}$ heteropolyacid of Example D was dissolved in 50 ml of water. 1.63 g of Cesium Carbonate (Aldrich Chemicals, Milwaukee, Wis.) was added to completely neutralize and precipitate the heteropolyacid, which was then filtered and dried. This catalyst was inactive under conditions described in Example 2.

Comparative Example H

Preparation of $H_4SiMo_{12}O_{40}$

A procedure was followed from the Journal of Less-Common Metals, 36, (1974), 77–93. To a 350 ml solution of 1,4-dioxane was added concentrated hydrochloric acid (80 ml) and water (75 ml) followed by slow addition of a sodium silicate solution. 6.99 g of sodium silicate solution was used (29.6 wt % as $SiO_2$ from Power Silicates, Augusta, Ga.). 100 g of sodium molybdate ($Na_2MoO_4 \cdot 2H_2O$, Aldrich, Ward Hill, Mass.) was added to 160 ml of $H_2O$ and was added to this mixture. This reaction mixture was allowed to stand for 24 hours. The acid was then prepared by exchanging the sodium salts with a strongly acidic sulfonic acid resin, Dowex 50X8-100 resin (Aldrich, Ward Hill, Mass.). The resultant acid was then dried.

Comparative Example I

Preparation of VPO Catalyst

A 3 liter round bottom flask was equipped with an addition funnel, mechanical stirrer and a reflux condenser. For the duration of the reflux, nitrogen gas was used to purge the apparatus. Vanadium pentoxide was air micronized prior to use. In an inert atmosphere Dry Box containing nitrogen gas, 99.8 g of vanadium pentoxide (Alrich Chemicals, Milwaukee, Wis.), 1034 ml of isobutyl alcohol (anhydrous, Aldrich Chemicals) and 95 ml of benzyl alcohol (anhydrous, Aldrich Chemicals) were added. The round bottom flask was then sealed off with a glass stopper and brought outside of the dry box. Anhydrous phosphoric acid was prepared in the inert atmosphere dry box by mixing 85.79 g of 85+% phosphoric acid (J. T. Baker and Co., Phillipsburg, N.J.) with 33.2 g of phosphorus pentoxide (J. T. Baker). The anhydrous phosphoric acid was then added to the addition funnel, brough outside of the dry box, and attached to the round bottom flask.

The vanadium pentoxide and alcohols were held at reflux temperatures for one hour. Anhydrous phosphoric acid was then added dropwise over a period of two hours. Following this procedure, the reflux continued for a period of fifteen additional hours. The precipitated solids are then filtered in a buchner funnel and dried in flowing nitrogen at 125° C. for a period of 16 hours.

Following this procedure, the precursor was directly calcined and activated in a small, 4 cm fluidized bed reactor, to generate the active vanadium pyrophosphate $(VO)_2P_2O_7$ catalyst phase by subjecting the precursor to the thermal conditions detailed below:

25°–390° C. in air
390° C. 1 hr in air
390° C. 1 hour in 1.5% butane/air
390°–460° C. 20 minutes 1.5% butane/air
460°–460° C. 18 hours 1.5% butane/air
460°–420° C. 1.5% butane/air
420°–360° C. 1.5% butane/air
360° C.–25° C. in $N_2$ Prior to activation, fine particles were sieved out by using a 400 mesh screen.

Description of Thermogravimetric Analysis (TGA) Test

A PL Thermal Sciences Thermogravimetric Analysis unit was used to measure weight gain of a catalyst during reoxidation, following a brief exposure to butane gas. The catalyst was exposed to 100% butane at 360° C. for a period of 5 minutes, at flow rate of 18 cc/min. Following that exposure, the TGA cup was purged with nitrogen gas for 20–30 minutes (60 cc/min). A 15% $O_2/N_2$ mixture was then admitted for a 40 minute reoxidation (60 cc/min). The weight gain of this reoxidation was plotted and compared to the VPO catalyst (without silica). One cycle was performed to obtain an initial indication of the "lattice oxygen capacity" of the catalyst. FIG. 1 is a graph of the percent weight gain of two catalysts versus time in minutes as described above. The top line labelled with a triangle represents catalyst of the present invention, $H_nPMo_{10}VCuO_{40}$ prepared as described in Example 1. The bottom line labelled with a circle represents the VPO catalyst prepared above.

Figure 2:
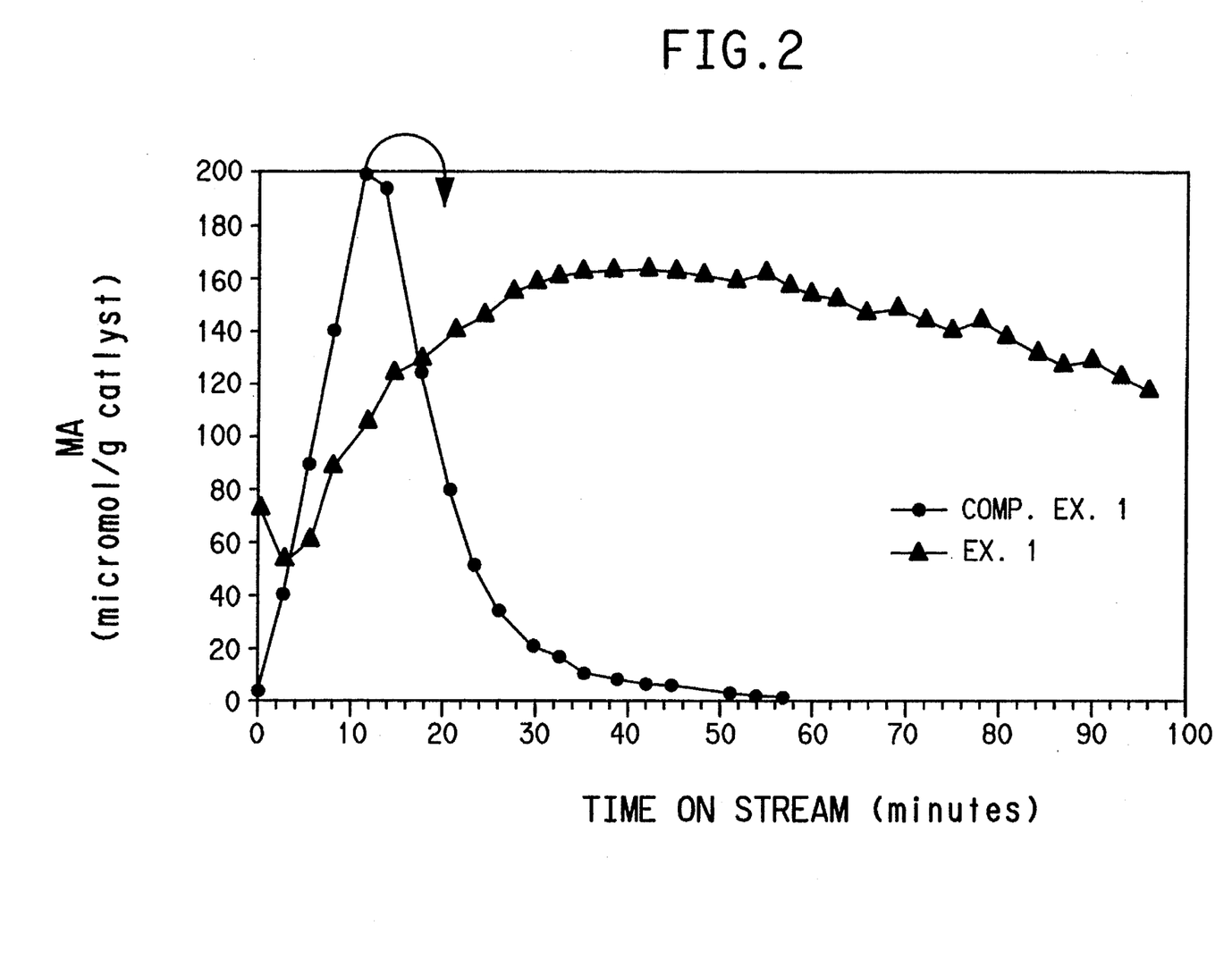
FIG. 2 is a graph of the maleic anhydride capacity in micromoles/g catalyst versus time on stream in minutes. The triangles and circles represent the same compounds as described above for FIG. 1.

Maleic anhydride formation was monitored using a Fisons Instruments Mass Spectrometer (available from VG/Fisons Instruments, Danver, Mass.) during the 5 minute exposure in butane. During that 5 minute exposure, the heteropolyacid, $H_nPMo_{10}VCuO_{40}$ appeared to produce a maleic anhydride signal lasting the full time period, unlike the VPO catalyst, as shown in FIG. 2 which is a graph of the maleic anhydride capacity in micromoles/g catalyst versus time on stream in minutes. Total maleic anhydride capacity for the $H_nPMo_{10}VCuO_{40}$ was 17 micromoles/g catalyst and 4–5 micromoles/g catalyst for the VPO catalyst. Tables III and IV show maleic anhydride capacity for other heteropolyacids of the present invention and other heteropolyacids found in the art.

Comparative Example J

Preparation of $H_5PMo_{10}V_2O_{40}$

In a 3 l flask, 88.28 g of ammonium molybdate was added $((NH_4)_6Mo_7O_{24} \cdot 4\,H_2O$, J. T. Baker) and 500 ml of water. In a separate beaker, 11.698 g of ammonium metavanadate ($NH_4VO_3$, Johnson-Matthey, Alfa) and 500 ml of water were added. When the solution was brought to a boil, the ammonium metavanadate slurry formed a solution. These were combined and 6.69 g of ammonium phosphate $(NH4)_2HPO_4$ was added, in addition to 55 ml of $NH_4OH$ (30%, J. T. Baker). The solution was exchanged with Dowex HCRW-2 resin to exchange the ammonium cations for the final heteropolyacid material, which was then dried as described in Example 1.

Comparative Example K

Preparation of $H_3PMo_{11}W_1O_{40}$

A procedure similar to that in Example 1 was followed. A 3 l reflux flask was employed. 1000 ml of water was added to 297.8 g of $MoO_3$ (Cerac), 25.02 g of $H_3PO_4$ (aqueous, J. T. Baker) and 45.46 g of tungstic acid, $H_2WO_4$ (Alfa). The solution was brought to a reflux to form the heteropolyacid. The water was removed and the samples were dried at 120° C. for approximately 12 hours, in nitrogen.

Comparative Example L

Preparation of $H_7P_2Mo_{17}VO_{62}$

A procedure similar to Example 1 was used, except the 122.35 g of $MoO_3$ (Johnson-Matthey-Alfa), 4.55 g of $V_2O_5$ (Alfa) and 11.53 g of 85% phosphoric acid (EM Sciences) was used.

TABLE I

Comparison of Microreactor Data for Various Heteropolyacids in 1.5% Butane/Air

| Example | Heteropolyacid | Activity k (sec$^{-1}$) | Selectivity to Maleic Anhydride at 40% Conversion |
|---|---|---|---|
| 1 | $H_nPMo_{10}VCuO_{40}$ | 1.41 | 45% |
| 3 | $H_8PMo_{10}VZnO_{40}$ | 0.6 | 43% |
| 4 | $H_8PMo_{10}VCoO_{40}$ | 0.21 | — |
| 5 | $H_8PMo_{10}VNiO_{40}$ | 0.36 | 26% |
| 6 | $H_nPMo_{10}VMn^zO_{40}$ | 0.17 | — |
| 7 | $H_nP_2Mo_{15}V_2CuO_{62}$ | 2.06 | 47% |
| 8 | $H_nPMo_9VCu_2O_{40}$ | 0.26 | 14% |
| 9 | $H_nPMo_9V_2CuO_{40}$ | 1.76 | 32% |
| 10 | $H_nP_2Mo_{14}V_2SbCuO_{62}$ | 2.57 | 47% |
| B | $H_4PMo_{11}VO_{40}$ (by reflux) | 0.22 | N.A.* |
| D | $H_4PMo_{11}VO_{40}$ (by exchange of sodium salts) | 0.63 | 41% |
| F | $H_3PMo_{12}O_{40}$ | 0.21 | — |
| G | $CsPMo_{11}VO_{40}$ | 0 | — |
| H | $H_4SiMo_{12}O_{40}$ | 0 | — |
| J | $H_5PMo_{10}V_2O_{40}$ | 1.90 | 33% |
| K | $H_3PMo_{11}WO_{40}$ | 0.29 | 0% |
| L | $H_7P_2Mo_{17}VO_{62}$ | 0.13 | — |

*40% conversion not attainable; 30% selectivity at 20% conversion

TABLE II

Comparison of Microreactor Data: Substituted Cu Heteropolyacid Compositions versus Addition of Cu to the Outside of the Heteropolyacid Cluster in 1.5% Butane/Air

| Example | Heteropolyacid | Activity k (sec$^{-1}$) | Selectivity to Maleic Anhydride at 40% Conversion |
|---|---|---|---|
| 1 | $H_nPMo_{10}VCuO_{40}$ | 1.41 | 45% |
| A | $Cu0.03/2V + H_3PMo_{12}O_{40}$ | — | 0% |
| C | $1\,Cu + H_4PMo_{11}VO_{40}$ | 0.44 | 34% |
| E | $1\,Cu + H_4PMo_{11}VO_{40}$ | 0.34 | 17% |

TABLE III

Comparison of MirrorReactor Data for Various Heteropolyacids

| Example | Heteropolyacid | Maleic Anhydride Capacity (μmoles/g catalyst) |
|---|---|---|
| 1 | $H_nPMo_{10}VCuO_{40}$ | 17 |
| 3 | $H_8PMo_{10}VZnO_{40}$ | 18 |
| 4 | $H_8PMo_{10}VCoO_{40}$ | 13 |
| 5 | $H_8PMo_{10}VNiO_{40}$ | 17 |
| 6 | $H_nPMo_{10}VMn^zO_{40}$ | 12 |
| 7 | $H_nP_2Mo_{15}V_2CuO_{62}$ | 16 |
| 8 | $H_nPMo_9VCu_2O_{40}$ | 12 |
| 9 | $H_nPMo_9V_2CuO_{40}$ | 18 |
| 10 | $H_nP_2Mo_{14}V_2SbCuO_{62}$ | 18 |
| B | $H_4PMo_{11}VO_{40}$ (by reflux) | 9.3 |
| D | $H_4PMo_{11}VO_{40}$ (by exchange of sodium salts) | 24 |
| F | $H_3PMo_{12}O_{40}$ | — |

TABLE III-continued

Comparison of MirrorAactor Data for Various Heteropolyacids

| Example | Heteropolyacid | Maleic Anhydride Capacity (μmoles/g catalyst) |
|---|---|---|
| H | $H_4SiMo_{12}O_{40}$ | — |
| J | $H_5PMo_{10}V_2O_{40}$ | 16 |
| K | $H_3PMo_{11}WO_{40}$ | 7 |
| L | $H_7P_2Mo_{17}VO_{62}$ | 15 |

TABLE IV

Comparison of Microreactor Data: Substituted Cu Heteropolyacid Compositions versus Addition of Cu to the Outside of the Heteropolyacid Cluster

| Example | Heteropolyacid | Maleic Anhydride Capacity (μmoles/g catalyst) |
|---|---|---|
| 1 | $H_nPMo_{10}VCuO_{40}$ | 17 |
| A | $Cu_{0.03}/2V + H_3PMo_{12}O_{40}$ | 0 |
| C | $1 Cu + H_4PMO_{11}VO_{40}$ | 12 |
| E | $1 Cu + H_4PMO_{11}VO_{40}$ | 3 |

What is claimed is:

1. A heteropolyacid catalyst for the oxidation of n-butane to maleic anhydride consisting essentially of crystalline oxide of formula I or formula II:

$$H_nPM_{12-x-y}V_xA^z_yO_{40} \quad (I)$$

$$H_nP_2M_{18-x-y}V_xA^z_yO_{62} \quad (II)$$

wherein:

P is a phosphorus heteroatom;

M independently is at least one metal in the +6 oxidation state selected from Mo and W, said metal occupying an octahedral site surrounding the phosphorus heteroatom;

x is an integer selected from 1, 2 and 3;

y is an integer selected from 1, 2 and 3;

A is at least one cation selected from the group consisting of Li, Mg, Sc, Ti, Cr, Mn, Fe, Co, Ni, Cu, Zn, Zr, Nb, Ru, Rh, Pd, Ta, Re, Os, It, Pt, Al, Ga, Ge, Sn, Pb, As, Sb, Bi, Po, Tb, and Pa, said cation occupying an octahedral site surrounding the phosphorus atom;

z is a number from 1–6 representing a weighted average of the oxidation states of all of the A cations; and n is a number calculated as follows in formula I: n=3−yz+x+6y, and in formula II: n=6+x+6y−yz.

2. The heteropolyacid catalyst of claim 1 wherein A is selected from the group consisting of Cu, Mn, Ni, Zn, Co, Sb, Bi, Pb, Fe, Pa, Pd and As.

3. The heteropolyacid catalyst of claim 2 wherein A is selected from the group consisting of Cu, Mn, Ni, Zn, Co, and Sb.

4. The heteropolyacid catalyst of claim 3 wherein A is Cu and Sb.

5. The heteropolyacid catalyst of claim 1 wherein said catalyst is the crystalline oxide of formula I.

6. The heteropolyacid catalyst of claim 1 wherein said catalyst is the crystalline oxide of formula II.

7. The heteropolyacid catalyst of claim 1 wherein M is Mo.

8. A process for the oxidation of n-butane to maleic anhydride comprising: contacting n-butane with a source of oxygen in the presence of a heteropolyacid catalyst consisting essentially of a crystalline oxide of formula I or formula II $$H_nPM_{12-x-y}V_xA^z_yO_{40} \quad (I)$$

$$H_nP_2M_{18-x-y}V_xA^z_yO_{62} \quad (II)$$

wherein:

P is a phosphorus heteroatom;

M is at least one metal in the +6 oxidation state selected from Mo and W, said metal occupying an octahedral site surrounding the phosphorus atom;

x is an integer selected from 1, 2 and 3;

y is an integer selected from 1, 2 and 3;

A is at least one cation selected from the group consisting of Li, Mg, Sc, Ti, Cr, Mn, Fe, Co, Ni, Cu, Zn, Zr, Nb, Ru, Rh, Pd, Ta, Re, Os, Ir, Pt, Al, Ga, Ge, Sn, Pb, As, Sb, Bi, Po, Tb, and Pa, said cation occupying an octahedral site surrounding the phosphorus heteroatom;

z is a number from 1–6 representing a weighted average of the oxidation states of all of the A cations; and n is a number calculated as follows formula I: n=3−yz+ x+6y, and in formula II: n=6+x+6y−yz.

9. The process of claim 8 wherein the catalyst is the only source of oxygen.

* * * * *